(12) United States Patent
Stensrud

(10) Patent No.: US 9,422,304 B2
(45) Date of Patent: Aug. 23, 2016

(54) SYNTHESIS OF ISOHEXIDE DICARBAMATES AND DERIVATIVES THEREOF

(71) Applicant: ARCHER DANIELS MIDLAND COMPANY, Decatur, IL (US)

(72) Inventor: Kenneth Stensrud, Decatur, IL (US)

(73) Assignee: Archer Daniels Midland Company, Decatur, IL (US)

(*) Notice: Subject to any disclaimer, the term of this patent is extended or adjusted under 35 U.S.C. 154(b) by 0 days.

(21) Appl. No.: 14/781,362

(22) PCT Filed: May 7, 2014

(86) PCT No.: PCT/US2014/037049
§ 371 (c)(1),
(2) Date: Sep. 30, 2015

(87) PCT Pub. No.: WO2014/200637
PCT Pub. Date: Dec. 18, 2014

(65) Prior Publication Data
US 2016/0083396 A1    Mar. 24, 2016

Related U.S. Application Data

(60) Provisional application No. 61/833,951, filed on Jun. 12, 2013.

(51) Int. Cl.
*A61K 31/34* (2006.01)
*C07D 493/04* (2006.01)
*A61K 31/40* (2006.01)
*C07D 307/12* (2006.01)
*C07D 307/42* (2006.01)
*C08G 71/04* (2006.01)
*C08G 73/00* (2006.01)
*A61K 47/26* (2006.01)
*A61K 31/428* (2006.01)
*A61K 31/343* (2006.01)

(52) U.S. Cl.
CPC .............. *C07D 493/04* (2013.01); *A61K 31/40* (2013.01); *C07D 307/12* (2013.01); *C07D 307/42* (2013.01); *C08G 71/04* (2013.01); *C08G 73/00* (2013.01); *A61K 31/343* (2013.01); *A61K 31/428* (2013.01); *A61K 47/26* (2013.01)

(58) Field of Classification Search
CPC ..... A61K 31/343; A61K 31/40; A61K 47/26; A61K 31/428
See application file for complete search history.

(56) References Cited

U.S. PATENT DOCUMENTS 4,169,152 A * 9/1979 LeMaistre ............ C07D 493/04
514/470

\* cited by examiner

*Primary Examiner* — Gregory Listvoyb
(74) *Attorney, Agent, or Firm* — Vincent Kung

(57) ABSTRACT

Isohexide dicarbamates and a method of preparing the same are described. The method involves reacting a mixture of an isohexide and a cynate salt in a non-aqueous solvent, with a miscible acid having a pKa of about 3.7 or less. The isohexide dicarbamates can serve as precursor materials from which various derivative compounds can be synthesized.

12 Claims, No Drawings

SYNTHESIS OF ISOHEXIDE DICARBAMATES AND DERIVATIVES THEREOF

BENEFIT OF PRIORITY

The present application claims benefit of priority from International Application No. PCT/US2014/037049, filed May 7, 2014, which claims priority to U.S. Provisional Application No. 61/833,951, filed Jun. 12, 2013, the entire contents of each are herein incorporated by reference.

FIELD OF INVENTION

The present invention relates to a synthesis of precursor compounds for plastics and other polymers. In particular, the present invention pertains to a method for preparing dicarbamates of 1,4:3,6-dianhydrohexitols, and derivative compounds of such dicarbamates.

BACKGROUND

Traditionally, polymers and commodity chemicals have been prepared from petroleum-derived feedstock. As petroleum supplies have become increasingly costly and difficult to access, interest and research has increased to develop renewable or "green" alternative materials from biologically-derived sources for chemicals that will serve as commercially acceptable alternatives to conventional, petroleum-based or -derived counterparts, or for producing the same materials as produced from fossil, non-renewable sources.

One of the most abundant kinds of biologically-derived or renewable alternative feedstock for such materials is carbohydrates. Carbohydrates, however, are generally unsuited to current high temperature industrial processes. Compared to petroleum-based, hydrophobic aliphatic or aromatic feedstocks with a low degree of functionalization, carbohydrates such as polysaccharides are complex, over-functionalized hydrophilic materials. As a consequence, researchers have sought to produce biologically-based chemicals that can be derived from carbohydrates, but which are less highly functionalized, including more stable bi-functional compounds, such as 2,5-furandicarboxylic acid (FDCA), levulinic acid, and 1,4:3,6-dianhydrohexitols.

1,4:3,6-Dianhydrohexitols (also referred to herein as isohexides) are derived from renewable, cereal-based polysaccharides. Isohexides embody a class of bicyclic furanodiols that derive from the corresponding reduced sugar alcohols (D-sorbitol, D-mannitol, and D-iditol respectively). Depending on the chirality, three isomers of the isohexides exist, namely: A) isosorbide, B) isomannide, and C) isoidide, respectively; the structures of which are illustrated in Scheme 1.

Scheme 1:

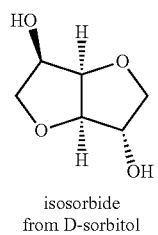

isosorbide
from D-sorbitol

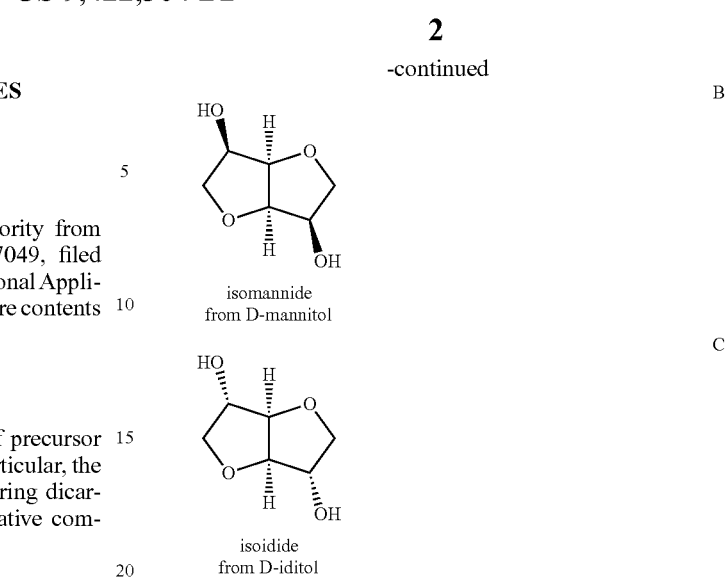

isomannide
from D-mannitol isoidide
from D-iditol

The isohexides are composed of two cis-fused tetrahydrofuran rings, nearly planar and V-shaped with a 120° angle between rings. The hydroxyl groups are situated at carbons 2 and 5 and positioned on either inside or outside the V-shaped molecule. They are designated, respectively, as endo or exo. Isoidide has two exo hydroxyl groups, while the hydroxyl groups are both endo in isomannide, and one exo and one endo hydroxyl group in isosorbide. The presence of the exo substituents increases the stability of the cycle to which it is attached. Also exo and endo groups exhibit different reactivities since they are more or less accessible depending on the steric requirements of the derivatizing reaction.

As a class of sugar-derived bifunctional hexahydrofurofurans, isohexides have received considerable interest and are recognized as valuable, organic chemical scaffolds that can serve as renewable surrogates to petrochemical compounds for a variety of uses, including plasticizers, surfactants, dispersants, lubricants, binders, paints, pharmaceuticals, and chiral auxiliaries. Some beneficial attributes include relative facility of their preparation and purification, the inherent economy of the parent feedstocks used, owing not only to their renewable biomass origins, which affords great potential as surrogates for non-renewable petrochemicals, but perhaps most significantly the intrinsic chiral bifunctionalities that permit a virtually limitless expansion of derivatives to be designed and synthesized.

As interest in chemicals derived from natural resources is increases, potential industrial applications have generated interest in the production and use of isohexides. For instance, in the field of polymeric materials, the industrial applications have included use of these diols to synthesize or modify polycondensates. Their attractive features as monomers are linked to their rigidity, chirality, non-toxicity, and the fact that they are not derived from petroleum. For these reasons, the synthesis of high glass transition temperature polymers with good thermo-mechanical resistance and/or with special optical properties is possible. Also the innocuous character of the molecules opens the possibility of applications in packaging or medical devices. For instance, production of isosorbide at the industrial scale with a purity satisfying the requirements for polymer synthesis suggests that isosorbide can soon emerge in industrial polymer applications. (See e.g., F. Fenouillot et al., "Polymers From Renewable 1,4:3,6-Dianhydrohexitols (Isosorbide, Isomannide and Isoidide): A Review," PROGRESS IN POLYMER SCIENCE, vol. 35, pp. 578-622

(2010), or X. Feng et al., "Sugar-based Chemicals for Environmentally sustainable Applications," CONTEMPORARY SCIENCE OF POLYMERIC MATERIALS, Am. Chem. Society, December 2010, contents of which are incorporated herein by reference.)

One use for isohexides (e.g., particularly isosorbide) is as monomers in homo- and copolymers. For example, isosorbide can be directly inserted at low concentrations into polyesters such as polyethylene terephthalate (PET), the effect of which is to make the PET chains more rigid and thus raise the glass transition temperature of PET, permitting higher temperature implementation. Furthermore, isosorbide polycarbonates, manufactured, for instance, in large scale by Roquette and Mitsubishi Chemical among others, offer augmented optical properties and enhanced durability to chemical, UV, and temperature degradation vs. conventional petroleum-derived analogs.

Similar to the aforementioned compounds, isosorbide-based polyurethanes have also received considerable attention as renewable, non-toxic materials, demonstrating, improved glass transition temperatures and thermal stabilities to an assortment of conventional petroleum-based variants.

To better take advantage of isohexides as a green feedstock, a clean and simple method of preparing the isohexides as a platform chemical or precursor that can be subsequently modified to synthesize other compounds would be welcome by those in the green or renewable chemicals industry.

SUMMARY OF THE INVENTION

The present invention relates, in part, to a method of synthesizing and isolating isohexide dicarbamates. The method involves providing a mixture of an isohexide with a cyanate salt in an inert organic solvent, reacting the mixture with an acid having a $pK_a$ less than or equal to about 3.7. The isohexide is at least one of the following: a) isosorbide, b) isomannide, and c) isoidide. The acid is added to the reaction mixture at a controlled rate of about 0.03-0.1 stoichiometric equivalents per minute.

In another aspect, the present invention pertains to the isohexide dicarbamates produced from the method.

In yet another aspect, the present invention pertains to processes for making certain derivatized materials that contain the isohexide dicarbamates as a structural substituent of non-polymer compounds, or as a monomer in either homopolymers or copolymers, and the derivative materials themselves.

DETAILED DESCRIPTION OF THE INVENTION

Section I

Definition

As used herein the following definitions are applicable:

The term "monomer" refers to a repeating structural unit of a polymer. A monomer typically is a lower molecular weight compound that can form covalent chemical bonds with other monomers, resulting in a polymer.

The term "polymer" refers to a compound comprising repeating structural units (monomers) connected by covalent chemical bonds, and which may include oligomers. Polymers may be derivatized (for example by hydrolysis), cross-linked, grafted, or end-capped. Non-limiting examples of polymers may include homopolymers, non-homopolymers, block copolymers, terpolymers, tetra-polymers, and homologues. A polymer may be a random, block, or an alternating polymer, or a polymer with mixed ransom, block, and/or alternating structure.

The term "homopolymer" refers to a polymer composed of a single type of repeating structural unit (monomers).

The term "non-homopolymer" refers to a polymer having more than one type of repeating structural units (monomers).

The term "copolymer" refers to a non-homopolymer composed of two or more types of repeating structural units (monomers), such as a "terpolymer" or "tetra-polymer," respectively, with three or four types of repeating structural units (monomers).

The term "derivative" refers to a material or chemical compound that is prepared as a secondary or tertiary reaction product from a primary structural substituent (for non-polymer compounds), or a monomer or polymer compound, in which the primary structural substituent, monomer or polymer has been modified in terms of either a functional group, structural moiety, or chemical linkage.

The term "water-tolerant Lewis acids" refers to a phenomenologic property of certain Lewis acid catalysts that are not deactivated by the presence of water, contrary to conventional Lewis acids that are summarily deactivated by reaction with water. Hence, a particular Lewis acid may show water tolerance for the purpose of one reaction, but not toward another reaction. (See e.g., S. Kobayashi, S. Nagayama, & T. Busujima, "Lewis Acid Catalysts Stable in Water: Correlation Between Catalytic Activity in Water and Hydrolysis Constants and Exchange Rate Constants for Substitution of Inner-Sphere Water Ligands," *J. Am. Chem. Soc.*, 120(32): 8287-8288 (1998); S. Kobayashi & I. Hachiya, "Lanthanide Triflates as Water-Tolerant Lewis Acids: Activation of Commercial Formaldehyde Solution and Use in the Aldol Reaction of Silyl Enol Ethers with Aldehydes in Aqueous Media," *The Journal of Organic Chemistry*, 59(13): 3590-3596, July 1994; N. A. Rebacz, "Hydration and Hydrolysis with Water Tolerant Lewis Acid Catalysis in High Temperature Water," Ph.D. Dissertation, University of Michigan (2011), the contents of which are incorporated herein by reference.)

Section II

Description

As biomass derived compounds that afford great potential as surrogates for non-renewable petrochemicals, 1,4:3,6-dianhydrohexitols are a class of bicyclic furanodiols that are valued as renewable molecular entities. (For sake of convenience, 1,4:3,6-dianhydrohexitols will be referred to as "isohexides" in the Description hereinafter.) As referred to above, the isohexides are good chemical platforms that have recently received interest because of their intrinsic chiral bifunctionalities, which can permit a significant expansion of both existing and new derivative compounds that can be synthesized.

Isohexide starting materials can be obtained by known methods of making respectively isosorbide, isomannide, or isoidide. Isosorbide and isomannide can be derived from the dehydration of the corresponding sugar alcohols, D-sorbitol and D mannitol. As a commercial product, isosorbide is also available easily from a manufacturer. The third isomer, isoidide, can be produced from L-idose, which rarely exists in nature and cannot be extracted from vegetal biomass. For this reason, researchers have been actively exploring different synthesis methodologies for isoidide. For example, the isoidide starting material can be prepared by epimerization from isosorbide. In L. W. Wright, J. D. Brandner, *J. Org. Chem.*, 1964, 29 (10), pp. 2979-2982, epimerization is induced by means of Ni catalysis, using nickel supported on diatomaceous earth. The reaction is conducted under relatively severe conditions, such as a temperature of 220° C. to 240° C. at a pressure of 150 atmosphere. The reaction reaches a steady state after about two hours, with an equilibrium mixture containing isoidide (57-60%), isosorbide (30-36%) and isomannide (5-7-8%). Comparable results were obtained when starting from isoidide or isomannide. Increasing the pH to 10-11 was found to have an accelerating effect, as well as increasing the temperature and nickel catalyst concentration. A similar disclosure can be found in U.S. Pat. No. 3,023,223, which proposes to isomerize isosorbide or isomannide. More recently, P. Fuertes proposed a method for obtaining L-iditol (precursor for isoidide), by chromatographic fractionation of mixtures of L-iditol and L-sorbose (U.S. Patent Publication No. 2006/0096588; U.S. Pat. No. 7,674,381 B2). L-iditol is prepared starting from sorbitol. In a first step sorbitol is converted by fermentation into L-sorbose, which is subsequently hydrogenated into a mixture of D-sorbitol and L-iditol. This mixture is then converted into a mixture of L-iditol and L-sorbose. After separation from the L-sorbose, the L-iditol can be converted into isoidide. Thus, sorbitol is converted into isoidide in a four-step reaction, in a yield of about 50%. (The contents of the cited references are incorporated herein by reference.)

A.—Preparation of Isohexide Dicarbamates

The method for preparing dicarbamates of isohexides (1,4: 3,6-dianhydrohexitols), as described herein, is a mild, high-yielding, single-step synthesis process. The process involves reacting a mixture of an isohexide and a cyanate salt in an inert organic solvent with an acid having a $pK_a$ of about 3.7 or less.

The present synthesis process can result in yields of corresponding dicarbamates of isohexides, as demonstrated in the accompanying examples. The process is able to produce isohexide dicarbmates in reasonably high molar yields of at least 55% from the isohexide and cyanate starting materials, typically about 60% or 70% to about 75% or 80%. With proper control of the reaction conditions and time, one can achieve a yield of about 82%-95% or better of the dicarbamates. The isohexides can be obtained either commercially or synthesized from relatively inexpensive, widely-available biologically-derived feedstocks.

The amount of cyanate salt used should be in excess of the amount of isohexide. The range of cyanate to isohexide ratio in terms of mole percent is a minimum of 2:1 (i.e., one cyanate per —OH group of an isohexide), and up to about 4:1 or 5:1 for purposes of practicality. (There is no theoretical maximum ratio, as once the isohexide forms the dicarbamate no further reactions will occur. However, the more unreacted salts that is present in the reaction, the more concern one may have in removing the salts subsequently during an aqueous wash.)

The isohexide is at least one of the following: isosorbide, isomannide, isoidide, or a combination thereof. The respective isohexide isomers can be obtained either commercially or synthesized from relatively inexpensive, widely-available biologically-derived feedstocks.

The cationic counter-ion to the cyanate salt is at least one of the following: Na, K, Li, Ag, Hg, Al, Ca, Mg, Pb, Sn, Ti, Ni, Cs, Rb, Cu, Zn, Cd, In, Co, Ga, Ba, Pd, Pt, Tl, Fr, Sb, Ge, Sr, Be, V, Bi, Mo, Mn, Fe, Nb, Cr, Eu, organic cations of ammonium, pyridinium, and/or a combination thereof.

The method uses a non-aqueous reaction system with an organic solvent that enables the isohexides to be soluble and reactive with the acid. The organic solvent can be at least one of the following: methylene chloride, chloroform, carbon tetrachloride, benzene, toluene, xylenes, linear and/or branched alkanes, tetrahydrofuran, 1,4-dioxane, dimethylsulfoxide, acetonitrile, dimethylformamide, acetic acid, HMPT, nitromethane, pyridine, N-methyl pyrolidinone, dimethylacetamide, ethyl acetate, acetone, methyl tert-butyl ether, diethyl ether.

An acid that is miscible or soluble in the organic solvent and having a pKa less than or equal to about 3.7 can be employed in the present synthesis. An acid having a pKa≤3.7 will have a greater propensity to protonate the cyanate in situ to generate isosyanic acid, which is the active electrophilic species. The acid preferably has pKa of about 3.5 or less (e.g. about 2.5 or 2.7 to about 3.0 or 3.6; or about 2.6 or 2.8 to about 3.2 or 3.3) as in some examples. The acid can be either a) an organic acid or b) a mineral acid. Organic acids tend to have an enhanced solubility in an organic solvent (e.g., methylene chloride) which may make them more effective in the reaction; nevertheless, mineral acids can be just as effective. An organic acid can be: e.g., trifluoro-acetic acid (TFA), trichloro-acetic acid, oxalic acid, pyruvic acid, malonic acid, furamic acid, maleic acid, malic acid, tartaric acid, picric acid, electron deficient benzoic acids (mono, di, and tri-nitro, cyano, trifluoro), terephthalic acid, methanesulfonic acid, p-toluenesulfonic acid and trifluoromethylsulfonic acid. A mineral acid can be: e.g., sulfuric acid, hydrogen halides (HCl, HBr, HI), perchloric acid, phosphoric acid, and boric acid.

Introduction of the acid to the reaction system should be performed in a stead and controlled manner so as to maximize production of the target dicarbamate, while avoiding or minimizing the formation of undesired side products. The acid is added to the reaction mixture of isohexide at a rate of about 0.03-0.1 stoichiometric equivalents per minute. Acids with a pKa of 3.5 or greater should be added slowly, because of the exothennic nature of the reaction.

One can execute the synthesis reaction in a single vessel under relatively mild conditions at a temperature of up to about 50° C. or 55° C. In general, the reaction is conducted at a starting temperature in a range from about 0° C. to about 30° C. or 40° C. More typically, the initial reaction temperature is in a range from about 10° C. to about 35° C. In certain embodiments, the reaction is performed at about ambient room temperature (i.e., –18° C. to –25° C.) to about 20° C. or 22° C. higher than room temperature. Because of its exothermic nature, the reaction can generate an additional 10° C.-15° C. of heat over and above the initial reaction temperature. This phenomenon permits the reaction to proceed at lower initial temperatures.

An advantage of the present process is that in excess amounts of cyanate, the isohexide converts substantially or completely to its dicarbamate species, minimizing waste and any remaining amount of unreacted starting materials in the final product mixture that may need separation. Another advantage of the present method is that the synthesis process requires minimal purification. As the dicarbamates are formed, they will precipitate from the homogeneous reaction mixture, and can be easily filtered to separate them from solution. One can further purify the isohexide dicarbamates using a variety of different techniques; for example, in a protocol that involves simple filtration, washing, and drying under high vacuum.

The process is able to produce isohexide dicarbamates in reasonably high molar yields of at least 55% from the isohexide starting materials, up to near quantitative yields. Typically yields range from about 60% to about 70%, or more typically about 68% or 75% to about 80% or 83%. With proper control of the reaction conditions and time, one can achieve a yield of about 85% to about 94% or 95% or better of the dicarbamate, such as demonstrated in the accompanying examples. Scheme 2 illustrates the structure of the three isohexide dicarbamate species.

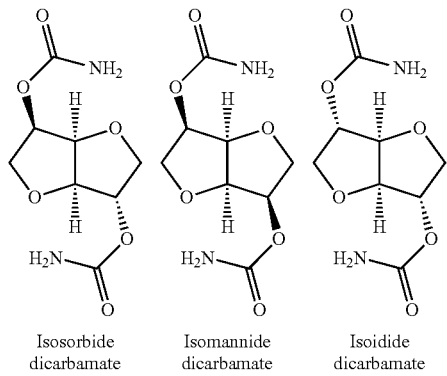

Scheme 2: Structure of the three isohexide dicarbamates.

Isosorbide dicarbamate    Isomannide dicarbamate    Isoidide dicarbamate

B.—Derivative Compounds of Isohexide Dicarbamate

Isohexide dicarbamates are useful and valuable precursor chemical compounds for a variety of potential products, including for instance, a broad range of polymers (e.g., polyurethanes), chiral auxiliaries (e.g., for asymmetric synthesis used in pharmaceutical production), surfactants, or solvents. The present carbamate compounds can be adapted to serve as either a new, bio-derived monomer or a replacement for existing structurally analogous compounds, such as used in the pharmaceutical, personal care, or industrial chemical (derived from fossil hydrocarbons) industries.

Some of the uses to which carbamates can be adapted are illustrated generally in the following list, which includes examples of carbamates used as monomer units in various kinds of polymer compounds or compositions: 1) U.S. 2004/0087728 A1 or U.S. 2005/0080196 (a curable surface coating composition containing a carbamate functional addition polymer); 2) U.S. 2013/0090443 (polymerization of carbamate and thiocarbamate compounds for cosmetic, skin or hair care, or other personal care compositions); 3) U.S. 2002/0119320 or U.S. 2004/0236031 (coating composition containing a carbamate-functional group or resin); 4) U.S. Pat. No. 3,165,498 (polyfunctional interpolymers of olefinically unsaturated carbamates and olefins, which have a plurality of carbamate groups); or 5) U.S. 2012/0125800 (polymer with a polyester-carbamate backbone and one or more blocked isocyanate groups and coating composition).

Scheme 3 presents, for example, representative derivative compounds that may be made from an isohexide dicarbamate; in particular, several derivative compounds that can be prepared from isosorbide dicarbamate. Although not shown, analog derivative compounds of isomannide and isoidide dicarbamates, as well as similar reactions to prepare such derivative compounds are also contemplated herein.

Scheme 3: Synthesis of Derivative Compounds from Isosorbide Dicarbamates

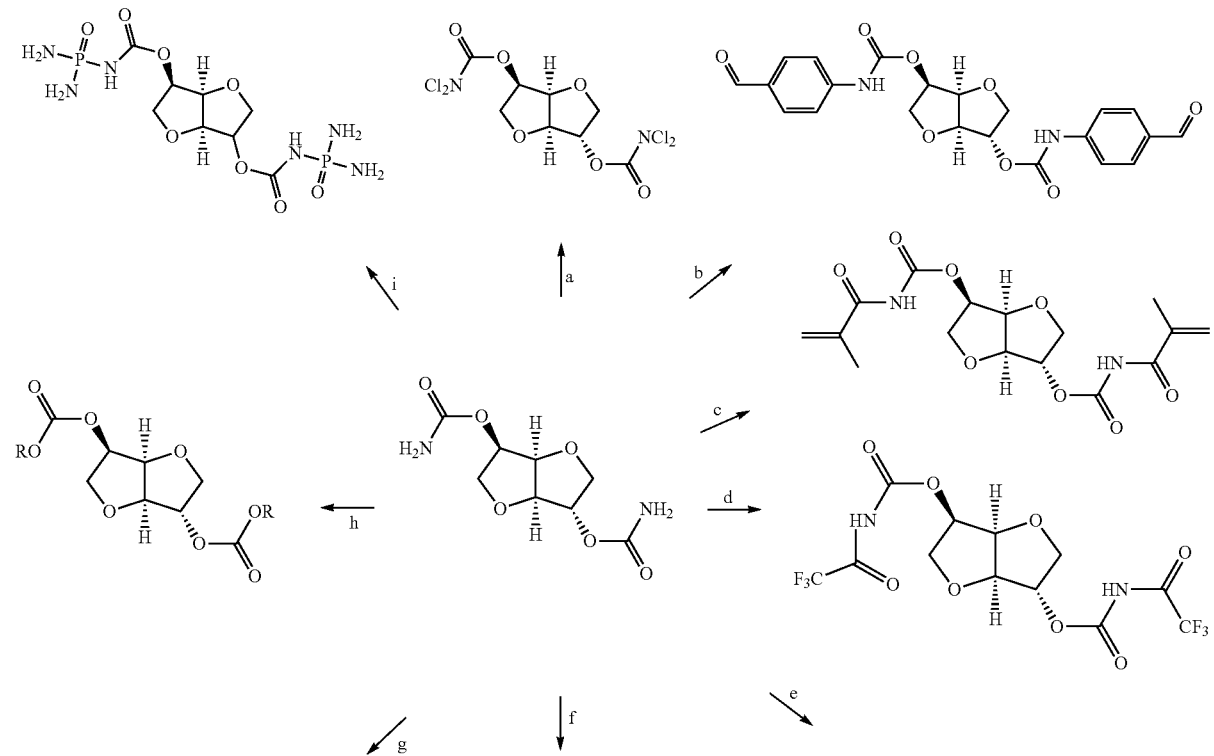

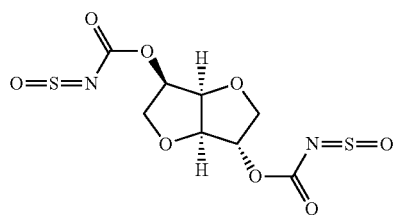 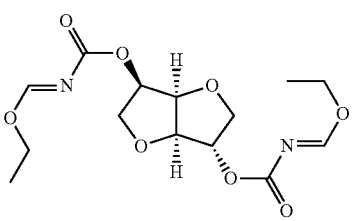

Proceeding clockwise, each of the example reactions (a-i) shown in Scheme 3, can be executed respectively using, for instance, the following reagents:

a) for (3R,3aR,6S,6aR)-hexahydrofuro[3,2-b]furan-3,6-diyl bis((113-dichloranylidene)carbamate): NaOCl, AcOH, $H_2O$;

b) for (3R,3aR,6S,6aR)-hexahydrofuro[3,2-b]furan-3,6-diyl bis((4-formylphenyl)carbamate): p-bromobenzaldehyde, $Cs_2CO_3$, $Pd(OAc)_2$, 4,5-Bis(diphenylphosphino)-9,9-dimethylxanthene, THF;

c) for (3R,3aR,6S,6aR)-hexahydrofuro[3,2-b]furan-3,6-diyl bis(methacryloylcarbamate): Methacryloyl chloride, t-BuOK, THF;

d) for (3R,3aR,6S,6aR)-hexahydrofuro[3,2-b]furan-3,6-diyl bis((2,2,2-trifluoroacetyl)carbamate): Trifluoroacetic anhydride, $Et_2O$;

e) for (3R,3aR,6S,6aR)-hexahydrofuro[3,2-b]furan-3,6-diyl bis(tert-butylcarbamate): 2-Methylpropene, $BF_3$-$Et_2O$, $PhCH_3$;

f) for diethyl N',N'''-(((((3R,3aR,6S,6aR)-hexahydrofuro[3,2-b]furan-3,6-diyl)bis(oxy))bis(carbonyl))-(1E,1'E)-diformimidate: Triethyl orthoformate, $BF_3$-THF, THF;

g) for (3R,3aR,6S,6aR)-hexahydrofuro[3,2-b]furan-3,6-diyl bis((oxo-$\lambda^4$-sulfanylidene)carbamate): $SOCl_2$;

h) for (3R,3aR,6S,6aR)-hexahydrofuro[3,2-b]furan-3,6-diyl dimethyl bis(carbonate): Lewis acids (e.g., $Bi(OTf)_3$, $Ga(OTf)_3$, $Sc(OTf)_3$, $In(OTf)_3$, $Cu(OTf)_3$, $Al(OTf)_3$, Lanthanide triflates), $CH_3OH$, $-180$-$220°$ C.;

i) for (3R,3aR,6S,6aR)-hexahydrofuro[3,2-b]furan-3,6-diyl bis((diaminophosphoryl)carbamate) in step 1) $PCl_5$, $CHCl_3$; step 2) $H_2O$, 0° C.; step 3) $NH_3$, $Et_3N$, $CHCl_3$, reflux. The particular time and temperatures will vary for each of the reaction processes, and can be determined empirically.

Another example of a derivative synthesis reaction that employs the isohexide dicarbamates described herein is shown in Scheme 4, which involves preparing formaldehyde polymers. (The reaction is expounded further in the accompanying Example 4.)

Scheme 4: Synthesis of Formaldehyde Polymers of Isohexide Decarbamates

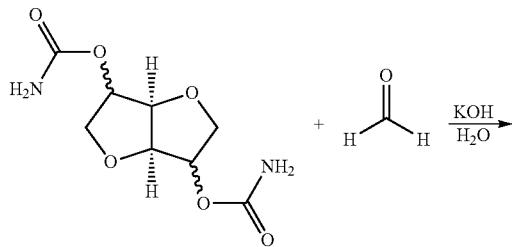

-continued

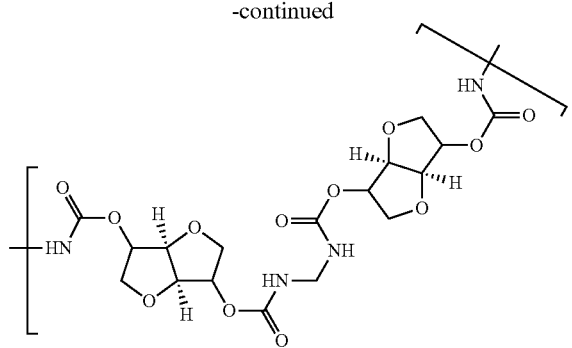

The formaldehyde-isohexide dicarbamate polymers would have applications (e.g., thermosetting resins) similar to, for instance, that described in U.S. 2009/0149608 (thermosetting resin composition with polycarbamate and polycarbamides reacted with formaldehyde), or Moon G. Kim, "Renewable Polyol-based Polycarbamates and Polycarbamate-Formaldehyde Thermosetting Resins," JOURNAL OF APPLIED POLYMER SCIENCE, 122(4), 2209-2220 (15 Jun. 2011), the contents of which are incorporated herein by reference.

Another possible useful application for the present isohexide dicarbamates can be as a monomer in an analogous method for crosslinking polyurethanes, such as described in U.S. 2011/0313091 (a crosslinked polyurethane composition having a polycarbamate as a first component and a polyaldehyde or acetal or hemi-acetal thereof as a second component), the content of which is incorporated herein by reference.

Furthermore, N-acylated carbamates can be useful platforms in the synthesis of biologically active compounds. The preparation and use of these derivative compounds are described, for example, by Liu, Xue-Kui, et al., ORGANIC & BIOMOLECULAR CHEMISTRY (2012), 10(6), 1275-1284; Kuhakarn, Chutima et al., TETRAHEDRON LETTERS (2007), 48(46), 8182-8184; Brouillette, Wayne J. et al., JOURNAL OF ORGANIC CHEMISTRY (1979), 44(5), 839-43, or in U.S. Pat. No. 3,819,683, relating to aryl N-methyl-N-acylcarbamates, the contents of which are incorporated herein by reference.

As an illustration of an alternative embodiment of a method for making derivatives, Scheme 5 shows a general reaction for a Lewis-acid-(LA)-triflate-mediated N-acylation of isohexide dicarbamates. Although Lewis acids have been employed for situations like N-acylation (e.g., Reddy, Chada Raji, et al., ARCHIVE FOR ORGANIC CHEMISTRY (ARKIVOC) 2008 (ii) 250-257), none have involved water-tolerant triflates and/or use a low quantity (≤1 or 2 mol. %) catalyst load (e.g., about 0.01 mol. % to about 1.5 mol. %) as in the present method and examples. In the present reactions, effective catalyst loads can range from as little as about 0.005 or 0.035 mol. % up to about 4 or 5 mol. %. Reaction times will tend to be longer with lower amounts, which can afford some degree of control in the reaction.

Scheme 5: N-acylation of isohexide dicarbamates

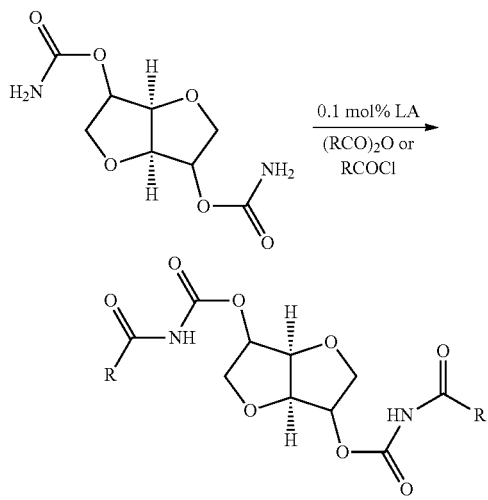

LA = Sc(OTf)₃, Bi(OTf)₃, Ga(OTf)₃, In(OTf)₃, Al(OTf)₃, Sn(OTf)₃
R = Alkyl, Aryl, Allyl The Lewis-acid triflate is water-tolerant, and thus useful as a homogeneous catalyst in an aqueous milieu. That is in other words, the Lewis acid triflate exhibits a uniquely stable behavior in water, in that it only very slowly hydrolyzes, and thus retains its acidity for a protracted time period when in the presence of water. For example, aluminum triflate is a powerful Lewis acid in an aqueous environment; while in contrast, aluminum chloride will hydrolyze immediately forming hydroxyl groups, and lose all of its acidic capacity. It is believed that a role of the Lewis-acid triflate is in lowering the activation barrier of the acid chloride or anhydride by coordinating to the carbonyl moiety. This action promotes a supervening displacement by the moderately nucleophilic isohexide dicarbamate to generate the N-acylated carbamate derivative compounds.

Scheme 6 illustrates a particular example of this reaction, involving N-acylation of isohexide dicarbamates with a bio-based fatty acid.

Scheme 6:

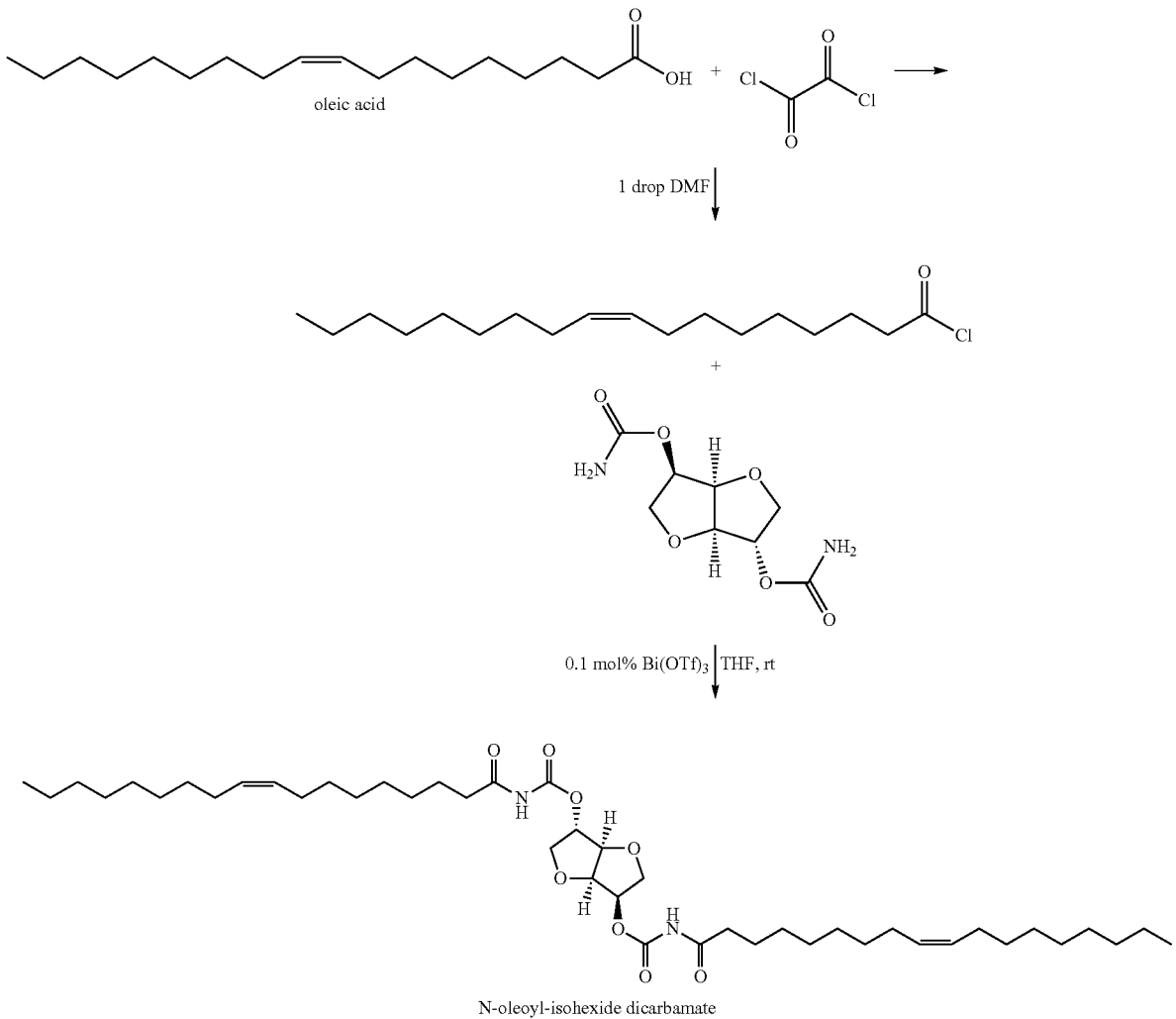

N-oleoyl-isohexide dicarbamate

The preparation of various derivative compounds according to this method of reaction will be described more fully in the accompanying examples below. Note that excess reagents will tend to generate undesired side reactions under the conditions employed. Hence, the ratio of reagents should be kept in a range, such as Example 4, about 5:1 maximum ratio of formaldehyde to isohexide dicarbamate, or as in Examples 5-7, about 2:1 ratio for reagent (not catalyst) to isohexide dicarbamate. The specific yield of derivative compounds will depend on the particular reactions. Typically, the yield of target derivative compound can range from at least about 50% or 55% up to about 93% or 97% or better.

Section III

Examples

The present invention is further illustrated with reference to the following examples.

A. Dicarbamates

Example 1

Synthesis of (3R,3aR,6S,6aR)-hexahydrofuro[3,2-b]furan-3,6-diyl dicarbamate, B (isosorbide dicarbamate)

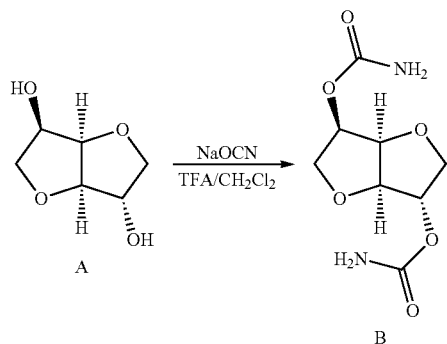

Experimental:

A three neck, 25 mL round bottomed flask equipped with an octagonal magnetic stir bar and internal temperature probe was charged with 1 g of isosorbide (6.84 mmol) A, 1.78 g of sodium cyanate (27.4 mmol) and 20 mL of methylene chloride. While stirring slowly, 2.32 mL of trifluoroacetic acid was added drop-wise over 10 minutes. The temperature of the mixture was seen to rise from 28° C. to 38° C., over approximately 20 minutes and then cool down to room temperature after 30 minutes. The reaction continued at room temperature for 2 more hours with slow stirring. After this time, a pasty white precipitate was observed, which was filtered, washed with three sequential 10 mL volumes of methylene chloride then water (salt removal) and dried under vacuum overnight, furnishing 1.43 g of a white powder (90.5%) corresponding to isosorbide dicarbamate B. The solid was shown to be insoluble in water and chloroform but readily dissolved in dimethylsulfoxide. $^1$H NMR (400 MHz, 10 mg in 1 mL d$^6$-DMSO) δ (ppm) 4.93-4.91 (m, 2H), 4.37-4.35 (m, 2H), 3.86-3.82 (m, 2H), 3.77-3.73 (m, 2H) (cf isosorbide in d$^6$-DMSO δ (ppm), 4.35-4.33 (m, 2H), 4.23 (dd, J=6.0 Hz, J=1.6 Hz, 2H), 4.10-4.07 (m, 2H), 3.67 (dd, J=5.2 Hz, J=2.2 Hz, 2H); $^{13}$C NMR (125 MHz, 10 mg in 1 mL of 1:1 D$_2$O/d$^6$-DMSO) δ (ppm), 158.83, 86.94, 82.46, 79.10, 74.19, 72.50, 71.94 (cf isosorbide in 1:1 D$_2$O/d$^6$-DMSO) δ (ppm), 88.74, 82.71, 76.79, 76.47, 73.15, 72.40. The signature $^{13}$C NMR resonance frequencies for trifluoroacetic acid, 162.22, 120.45 ppm, and sodium cyanate, 128.77 ppm (in 1:1 D$_2$O/d$^6$-DMSO) were noticeably absent.

Example 2

Synthesis of (3R,3aR,6R,6aR)-hexahydrofuro[3,2-b]furan-3,6-diyl dicarbamate, B (isomannide dicarbamate)

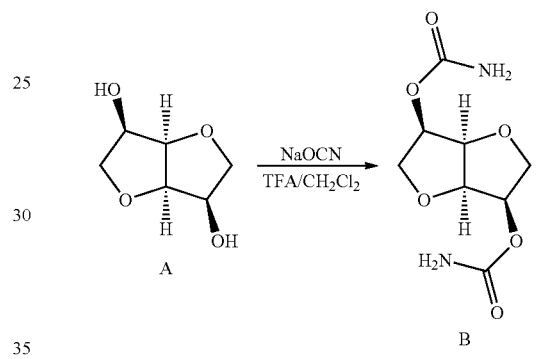

Experimental:

A three neck, 25 mL round bottomed flask equipped with an octagonal magnetic stir bar and internal temperature probe was charged with 1 g of isomannide (6.84 mmol) A, 1.78 g of sodium cyanate (27.4 mmol) and 20 mL of methylene chloride. While stirring slowly, 2.32 mL of trifluoroacetic acid was added dropwise over 10 minutes. The temperature of the mixture was seen to rise from 26° C. to 35° C., over approximately 18 minutes and then cool down to room temperature after 30 minutes. The reaction continued for 2 more hours at room temperature with slow stirring. After this time, a pasty white precipitate was observed, which was filtered, washed with three sequential 10 mL volumes of methylene chloride then water (salt removal) and dried under vacuum, affording 1.48 g of a light yellow powder (93.6% of theoretical) representing isomannide dicarbamate B. The solid was shown to be insoluble in water and chloroform but soluble in dimethylsulfoxide. $^1$H NMR (400 MHz, 10 mg in 1 mL d$^6$-DMSO) δ (ppm) 4.86-4.81 (m, 2H), 4.54 (d, J=6.4 Hz, 2H), 3.91-3.88 (dd, J=6.4 Hz, J=1.8 Hz, 2H), 3.61-3.59 (dd, J=5.2 Hz, J=2.0 Hz, 2H) (cf isomannide in d$^6$-DMSO) δ (ppm) 4.76 (d, J=5.8 Hz, 2H), 4.26-4.25 (m, 2H), 4.06-4.04 (dd, J=4.8 Hz, J=1.5 Hz, 2H), 3.36-3.34 (m, 2H); $^{13}$C NMR (125 MHz, 10 mg in 1.0 mL of 1:1 D$_2$O/d$^6$-DMSO) δ (ppm) 158.18, 81.63, 74.58, 71.12 ppm (cf isomannide in 1:1 D$_2$O/d$^6$-DMSO δ (ppm), 82.95, 73.33, 71.28. The signature $^{13}$C NMR resonance frequencies for trifluoroacetic acid, 162.22, 120.45 ppm, and sodium cyanate, 128.77 ppm (in 1:1 D$_2$O/d$^6$-DMSO) were noticeably absent.

Example 3

Synthesis of (3S,3aR,6S,6aR)-hexahydrofuro[3,2-b]furan-3,6-diyl dicarbamate, B (isoidide dicarbamate)

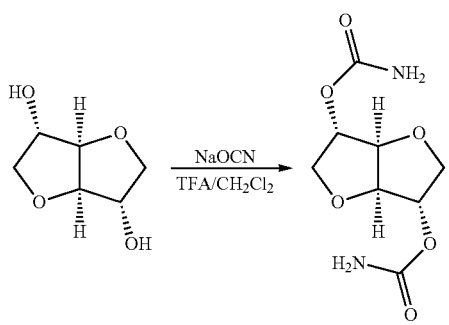

Experimental:

A three neck, 25 mL round bottomed flask equipped with an octagonal magnetic stir bar and internal temperature probe was charged with 1 g of isoidide (6.84 mmol) A, 1.78 g of sodium cyanate (27.4 mmol) and 20 mL of methylene chloride. While stirring slowly, 2.32 mL of trifluoroacetic acid was added drop-wise over 10 minutes. The temperature of the mixture was seen to rise from 27° C. to 35° C., over approximately 15 minutes and then cool down to room temperature after 30 minutes. The reaction continued at room temperature overnight with slow stirring. After this time, an off-white suspension was observed that was filtered, washed with three sequential 10 mL volumes of methylene chloride then water (salt removal) and dried under vacuum overnight, yielding 1.36 g of a beige powder (86.1%) that specified isoidide dicarbamate B. The solid was shown to be insoluble in water and chloroform but soluble in dimethylsulfoxide. $^1$H NMR (400 MHz, 10 mg in 1 mL d$^6$-DMSO) δ (ppm) 4.88 (d, J=4.8 Hz, 2H), 4.46 (s, 2H), 3.85-3.83 (m, 2H), 3.78-3.76 (d, J=4.45 Hz, 2H) (cf isoidide in d$^6$-DMSO) δ (ppm) 4.31 (s, 2H), 4.02-4.00 (dd, J=4.2 Hz, J=1.5 Hz, 2H) 3.64-3.59 (m, 4H); $^{13}$C NMR (125 MHz, 10 mg in 1.5 mL of 1:1 D$_2$O/d$^6$-DMSO) δ (ppm) 158.33, 86.15, 78.78, 73.17 (cf isoidide in 1:1 D$_2$O/ d$^6$-DMSO) δ (ppm) 87.95, 76.05, 75.27. The signature $^{13}$C NMR resonance frequencies for trifluoroacetic acid, 162.22, 120.45 ppm, and sodium cyanate, 128.77 ppm (in 1:1 D$_2$O/ d$^6$-DMSO), were noticeably absent.

B. Derivatives Compounds

Example 4

Synthesis of Isosorbide Dicarbamate-Formaldehyde Polymer

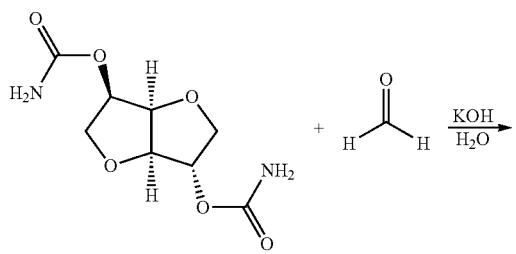

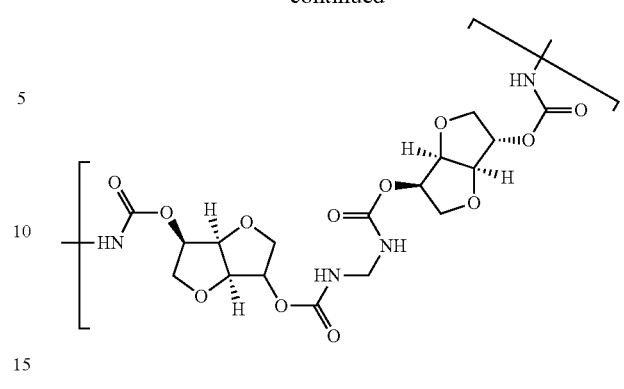

Experimental:

A single neck, 50 mL round bottomed flask equipped with a ½" PTFE coated magnetic stir bar was charged with 300 mg of a 50% solution of formaldehyde (5 mmol), 232 mg of isosorbide dicarbamate (1 mmol), 500 mL of water, and 1 N aqueous KOH until the pH was 8.5. While stirring, the resultant suspension was heated to 90° C.; after 30 min, the solution opacity disappeared, and the reaction continued for 30 more min. After this time, the pH was adjusted to 1.5 with 1N HCl and reaction proceeded until a viscosity change was apparent, at which time the reaction was culminated by cooling and pH adjusting to 8 with 1N KOH. Here the resin solids are measured.

In a particular embodiment, one can make derivative compound by the reaction of the present isohexide dicarbamates with Lewis acids. Scheme 7 depicts a generic reaction for N-acylation of dicarbamates with water-tolerant Lewis-acid (LA) triflates.

Scheme 7:

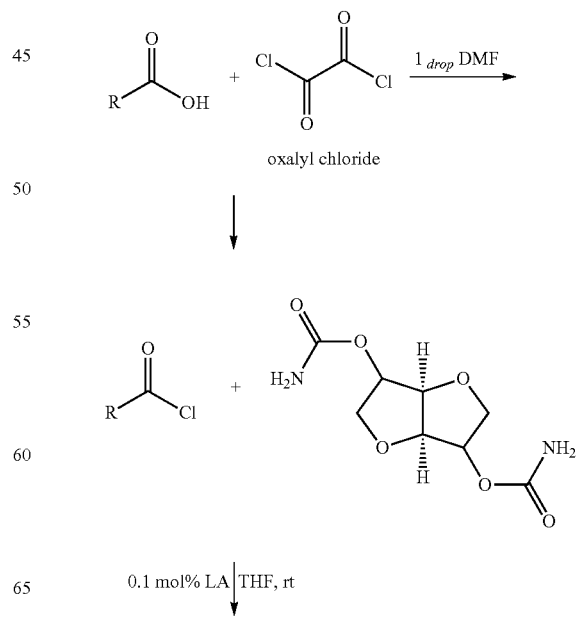

-continued

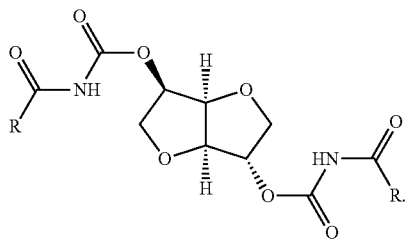

LA = Bi(OTf)₃, Sc(OTf)₃, Ga(OTf)₃, Sn(OTf)₂, In(OTf)₃, Al(OTf)₃, Cu(OTf)₂
R = alkyl, allyl, or aryl; rt = room temperature (e.g., ~18° C.-25° C.);
DMF (dimethylformamide); THF (tetrahydrofuran)

Example 5

Synthesis of (3R,3aR,6S,6aR)-hexahydrofuro[3,2-b]furan-3,6-diyl bis(acetylcarbamate)

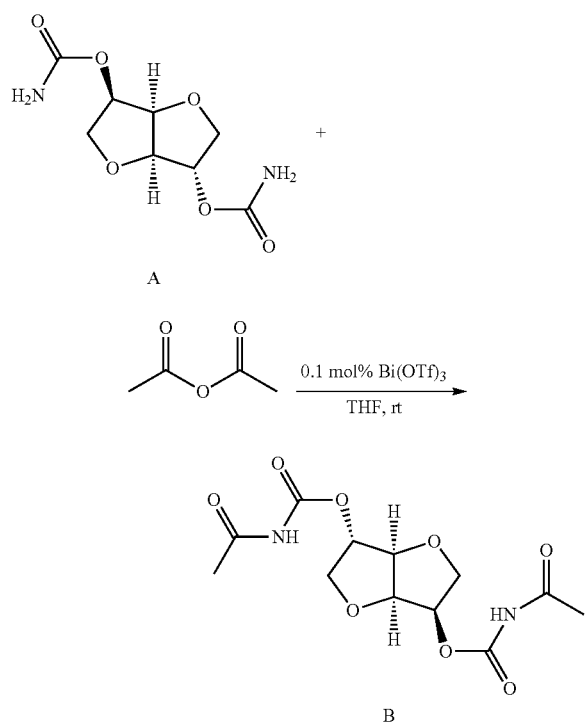

Experimental:

A 10 mL round bottomed flask equipped with a ¼" PTFE coated magnetic stir bar was charged with 300 mg of isosorbide dicarbamate A (1.29 mmol), 64 µg of Sc(OTf)₃ (0.1 mol %) and 2 mL of anhydrous THF. While stirring, 243 µL of acetic anhydride (2.58 mmol) was added dropwise over 15 minutes. The solution was observed to warm considerably with each drop. After the entire volume had been added, the mixture continued to stir at room temperature for an additional 4 hours. An aliquot was removed and spotted on a normal phase TLC plate, which revealed a single band (cerium molybdate illumination, Rf=0.41) after development in 100% EtOAc. The signature band corresponding to A, Rf=0.26, was noticeably absent, adducing that A had fully converted. Solids were then filtered and excess solvent was then evaporated under reduced pressure, affording 366 mg (90% of theory) of a beige semi-solid material analyzed by ¹³C NMR (100 MHz, d⁶-DMSO) δ (ppm) 168.2, 153.6, 94.6, 74.5, 62.1, 23.2 ppm.

Example 6

Synthesis of (3R,3aR,6S,6aR)-hexahydrofuro[3,2-b]furan-3,6-diyl bis(benzoylcarbamate), B

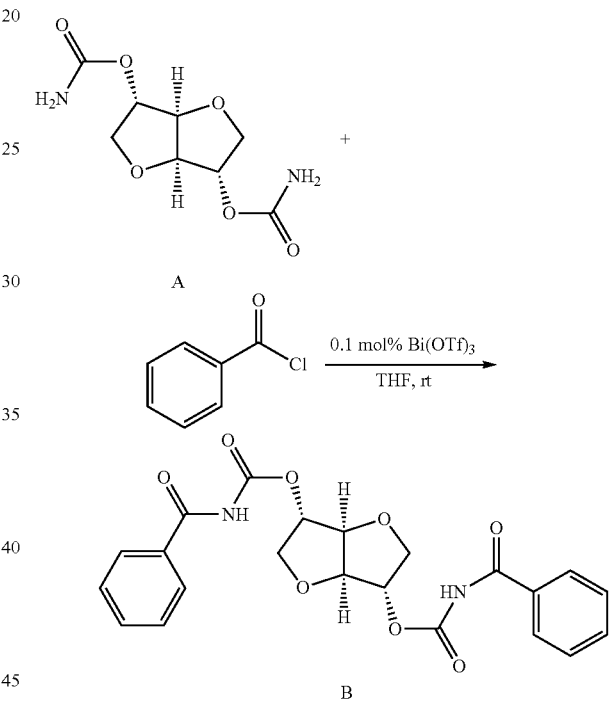

Experimental:

A 10 mL round bottomed flask equipped with a ¼" PTFE coated magnetic stir bar was charged with 300 mg of isoidide dicarbamate A (1.29 mmol), 85 µg of Sc(OTf)₃ (0.1 mol %) and 2 mL of anhydrous THF. While stirring, 299 µL of benzoyl chloride (2.58 mmol) was added dropwise over 15 minutes. The solution was observed to warm considerably with each drop. After the entire volume had been added, the mixture continued to stir at room temperature for an additional 4 hours. An aliquot was removed and spotted on a normal phase TLC plate, which revealed a single band (UV-Vis illumination, Rf=0.47) after development in 100% EtOAc. The signature band corresponding to A, Rf=0.21, was noticeably absent, adducing that A had fully converted. Solids were then filtered and excess solvent was then evaporated under reduced pressure, affording 505 mg (89% of theoretical) of a beige semi-solid material analyzed by ¹³C NMR (100 MHz, d⁶-DMSO) δ (ppm) 168.9, 152.9, 134.2, 131.3, 128.9, 128.1, 93.7, 72.9, 63.7, 22.5 ppm.

Example 7

Synthesis of (3R,3aR,6R,6aR)-hexahydrofuro[3,2-b]furan-3,6-diyl bis(acryloylcarbamate), B

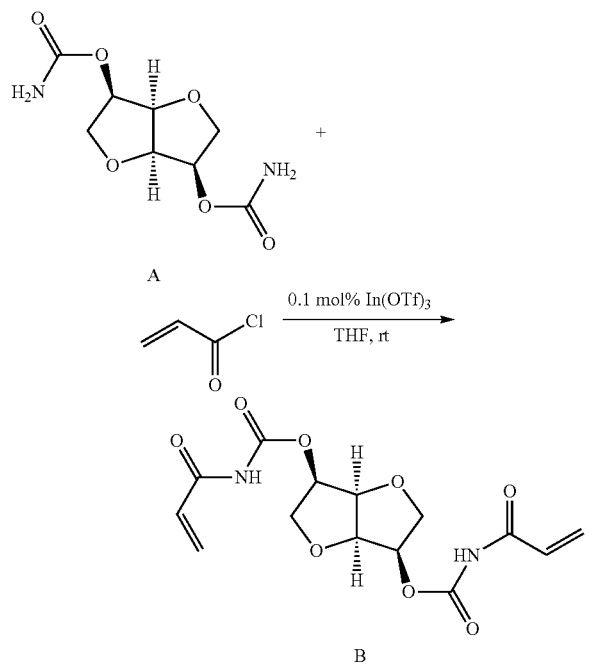

Experimental:

A 10 mL round bottomed flask equipped with a ¼" PTFE coated magnetic stir bar was charged with 300 mg of isomannide dicarbamate A (1.29 mmol), 73 g of In(OTf)$_3$ (0.1 mol %) and 2 mL of anhydrous THF. While stirring, 209 μL of propenoyl chloride (2.58 mmol) was carefully added, dropwise over 15 minutes. The solution was observed to warm considerably with each drop. After the entire volume had been added, the mixture continued to stir at room temperature for an additional 6 hours. An aliquot was removed and spotted on a normal phase TLC plate, which revealed a single band (cerium molybdate illumination, Rf=0.44) after development in 100% EtOAc. The signature band corresponding to A, Rf=0.29, was noticeably absent, adducing that A had fully converted. Solids were then filtered and excess solvent was then evaporated under reduced pressure, affording 350 mg (80% of theoretical) of a beige semi-solid material analyzed by $^{13}$C NMR (100 MHz, d$^6$-DMSO) δ (ppm) 169.7, 154.1, 132.5, 95.1, 74.6, 65.0, 23.6 ppm.

Although the present invention has been described generally and by way of examples, it is understood by those persons skilled in the art that the invention is not necessarily limited to the embodiments specifically disclosed, and that modifications and variations can be made without departing from the spirit and scope of the invention. Thus, unless changes otherwise depart from the scope of the invention as defined by the following claims, they should be construed as included herein.

I claim:

1. A process for preparing dicarbamates of 1,4:3,6-dianhydrohexitols, the process comprising: providing a mixture of an isohexide with a cyanate salt in an inert organic solvent, reacting said mixture with an acid having a pK$_a$≤3.7.

2. The process according to claim 1, wherein said acid is added to said reaction mixture of isohexide at a rate of about 0.03-0.1 stoichiometric equivalents per minute.

3. The process according to claim 1, wherein said isohexide is at least: a) isosorbide, b) isomannide, and c) isoidide.

4. The process according to claim 1, wherein said organic solvent at least: methylene chloride, chloroform, carbon tetrachloride, benzene, toluene, xylenes, linear and/or branched alkanes, tetrahydrofuran, 1,4-dioxane, dimethylsulfoxide, acetonitrile, dimethylformamide, acetic acid, HMPT, nitromethane, pyridine, N-methyl pyrolidinone, dimethylacetamide, ethyl acetate, acetone, methyl tert-butyl ether, diethyl ether.

5. The process according to claim 1, wherein said cyanate salt having a cationic counter-ion selected from the group consisting of: Na, K, Li, Ag, Hg, Al, Ca, Mg, Pb, Sn, Ti, Ni, Cs, Rb, Cu, Zn, Cd, In, Co, Ga, Ba, Pd, Pt, Tl, Fr, Sb, Ge, Sr, Be, V, Bi, Mo, Mn, Fe, Nb, Cr, Eu, organic cations of ammonium, pyridinium, and a combination of the foregoing.

6. The process according to claim 1, wherein said acid is either an organic acid or a mineral acid.

7. The process according to claim 6, wherein when said acid is an organic acid, said acid is at least: trifluoro-acetic acid (TFA) trichloro-acetic acid, oxalic acid, pyruvic acid, malonic acid, fumaric acid, maleic acid, malic acid, tartaric acid, picric acid, electron deficient benzoic acids (mono, di, and tri-nitro, cyano, trifluoro), terephthalic acid, methanesulfonic acid, p-toluenesulfonic acid, and trifluoromethylsulfonic acid.

8. The process according to claim 6, wherein when said acid is a mineral acid, said acid is at least: sulfuric acid, hydrogen halides (HCl, HBr, HI), perchloric acid, phosphoric acid, and boric acid.

9. The process according to claim 1, wherein said reaction is conducted at a temperature in a range from about 0° C. to about 55° C.

10. The process according to claim 1, further comprising purifying said isohexide dicarbamates according to a protocol involving a simple filtration, washing, and drying under high vacuum.

11. The process according to claim 1, wherein said process results in at least a 55% yield of corresponding isohexide dicarbamates.

12. The process according to claim 11, wherein said process results in about a 70% or greater yield of corresponding isohexide dicarbamates.

* * * * *